US006713611B2

(12) United States Patent
Pyo et al.

(10) Patent No.: US 6,713,611 B2
(45) Date of Patent: Mar. 30, 2004

(54) METHOD FOR REMOVING ENDOTOXIN FROM THE SAMPLES CONTAINING BASIC PROTEIN

(75) Inventors: Sang-Hyun Pyo, Taejeon (KR); Heung-Bok Park, Taejeon (KR); Jin-Eon So, Taejeon (KR); Jin-Hyun Kim, Taejeon (KR); Seung-Suh Hong, Taejeon (KR); Hyun-Soo Lee, Seoul (KR)

(73) Assignee: Samyang Genex Co., Seoul (KR)

( * ) Notice: Subject to any disclaimer, the term of this patent is extended or adjusted under 35 U.S.C. 154(b) by 0 days.

(21) Appl. No.: 09/948,491

(22) Filed: Sep. 6, 2001

(65) Prior Publication Data

US 2002/0147315 A1 Oct. 10, 2002

(30) Foreign Application Priority Data

Sep. 7, 2000 (KR) ........................................ 2000-52914

(51) Int. Cl.[7] ................................................ C07K 1/18
(52) U.S. Cl. ...................................... 530/415; 530/416
(58) Field of Search ................................. 530/415, 416

(56) References Cited

U.S. PATENT DOCUMENTS

| 4,808,314 A | * | 2/1989 | Karplus et al. ............. 210/638 |
| 5,019,502 A | * | 5/1991 | Rienstra et al. ............. 435/101 |
| 5,510,242 A | * | 4/1996 | Blais et al. ................ 435/7.32 |
| 5,530,100 A | * | 6/1996 | Darling et al. .............. 530/383 |
| 5,605,691 A | * | 2/1997 | Carroll .................... 424/184.1 |
| 5,747,663 A | | 5/1998 | Colpan et al. .............. 536/25.4 |
| 6,060,278 A | * | 5/2000 | Liu et al. .................... 435/69.1 |
| 6,428,703 B1 | * | 8/2002 | Zinn et al. .................. 210/635 |

FOREIGN PATENT DOCUMENTS

| FR | 2624011 A1 | * | 6/1989 | .......... A61K/09/08 |
| WO | WO 8903885 A1 | * | 5/1989 | ........... C12P/21/00 |

OTHER PUBLICATIONS

Petsch, D., et al., "Endotoxin removal from protein solutions," *Journal of Biotechnology*, vol. 76, pp. 97–119 (2000).

Aida, Yoshitomi, et al., "Removal of endotoxin from protein solutions by phase separation using Triton X–114," *Journal of Immunological Methods*, vol. 132, pp. 191–195 (1990).

* cited by examiner

*Primary Examiner*—Jon P. Weber
(74) *Attorney, Agent, or Firm*—Ladas & Parry

(57) ABSTRACT

The present invention relates to a method of removing an endotoxin from solution containing basic proteins. More specifically, the method of the present invention comprises the steps of adding the surfactant to solution containing the basic protein obtained from the recombinant microorganism and mixing the resultant, of loading the resultant solution on the cation exchange column, washing the cation exchange column with solution which does not contain surfactant, and eluting the basic protein of interest from the cation exchange column.

17 Claims, No Drawings

SEQUENCE LISTING

```
<160> NUMBER OF SEQ ID NOS: 4

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence: Primer
```

```
<400> SEQUENCE: 1
ggtgccaagg atccatgtcg gaaaccgctc ctgccga                              37

<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 2
ggtgccactc gagttacttc tttttggcag ccgc                                 34

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 3
gggcatatga tgtcggaaac cgctcctgcc ga                                   32

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 4
gggggatcct tacttctttt tggcagccgc                                      30
```

METHOD FOR REMOVING ENDOTOXIN FROM THE SAMPLES CONTAINING BASIC PROTEIN

CROSS REFERENCE TO RELATED APPLICATION

This application is based on application No. 2000-52914 filed in the Korean Industrial Property Office on Sep. 7, 2000, the content of which is incorporated hereinto by reference.

BACKGROUND OF THE INVENTION (a) Field of the Invention

The present invention relates to a method for removing endotoxin from the samples containing useful proteins.

(b) Description of the Related Art

One of the methods of mass production for basic proteins having medical activity is that the proteins are produced by using the recombinant microbial expression system. When using the recombinant microbial expression system, especially the system by using the bacteria as a host such as gram (−) bacteria, it is essential to sufficiently remove endotoxin which is a component of cell wall of the host in the purification step.

Endotoxin is a lipopolysaccharide in the cell wall of most gram-negative bacteria such as E.coli. Endotoxin included in proteins is known to cause symptoms of high fever, endotoxin shock, and inflammation even in a very small amount.

1) ion exchange chromatography, 2) affinity chromatography, 3) ultrafiltration, and 4) phase separation using surfactant have been presented to remove the endotoxin.

However, positively-charged basic proteins such as DNA binding proteins can bind to negatively-charged endotoxin through the electrostatic attractive force. Accordingly, Endotoxin cannot be sufficiently removed by ion exchange chromatography or affinity chromatography (Journal of Immunological Methods, vol. 132, pp.191–195, 1990).

Generally, in the ultrafiltration method, endotoxin is removed by using the membrane with 10K cut-off where molecules with smaller molecular weight than 10K pass through the membrane but endotoxin having greater molecular weight remain. However, in case that the material of interest to be removed is macromolecules such as protein, the ultrafiltration method is disadvantageous in that proteins can be lost and the removal efficiency is decreased, because the ultrafilteration process is repetitively preformed by using the membrane with 100K cut-off or more.

The removal method of endotoxin using the phase separation with surfactant is performed by adding surfactant to the protein solution, mixing the resultant, inducing the separation by centrfuging, and then removing the layer containing endotoxin. Though the above method has advantages in high removal efficiency of endotoxin, the disadvantageous need of additional steps is required to remove residual surfactant and the removal process should be performed repetitively. Thus, the yield of purification is decreased. In addition, considering that the temperature of solution must be maintained at 35° C. or higher in the method, it is not applicable to temperature-sensitive proteins.

U.S. Pat. No. 5,747,663 disclosed the method of removing endotoxin from the substrate solution where cell lysate was treated with triton X-114 and then with anion exchange chromatography. The endotoxin of 10–12 I.U/mg is still in the resultant solution.

SUMMARY OF THE INVENTION

The present invention provides a method whereby endotoxin is effectively removed to an extremely small amount, when the basic protein is separated or purified from the recombinant microorganism.

The present invention relates to the method of removing endotoxin from the sample solution containing the same. The method of present invention comprises the steps of:

(a) adding a detergent to solution containing the basic protein obtained from the recombinant microorganism, and mixing the resultant;

(b) loading the resulting solution on cation exchange resin;

(c) washing the cation exchange resin with solution which does not contain the detergent; and (d) eluting the basic protein of interest from the cation exchange resin.

By using the method of the present invention, endotoxin can be sufficiently removed from the basic proteins designated therapeutic use.

The method of the present invention is applicable to basic proteins or basic peptides which are purified partially or completely. Thus, depending on the need, the method can be used in the middle step or the final step of purification process.

The term, basic proteins, described herein is intended to mean a peptide or a protein which has the isoelectic point of 7.0 or higher. For examples, the basic proteins include the DNA-binding proteins such as histone, basic peptides with antibacterial activity such as buforin and magainin, and basic fibroblast growth factors, and the like.

The detergent for the present invention is preferably non-ionic detergent including Triton X-114, Triton X-110, Tween 80, Tween 20, and the like. The concentration of the detergent can be 0.01~10%(v/v), or more preferably 0.1~2.0%(v/v). When the concentration of detergent is lower, the removal efficiency of endotoxin is decreased. When the concentration is higher, it takes much time to remove residual detergent.

The cation exchange resin applicable to the present invention has no special limitation, and can be selected suitably depending on the kinds of basic proteins to be separated or purified. For examples, the cation exchange resin includes Streamline SP, CM-Sepharose FF, SP-Sepharose FF, Porus 20 HR, and the like.

As needed, to facilitate the separation of endotoxin from the basic protein solution, the solution containing basic protein is mixed with the added detergent, and then, the resulting solution can be left for a time period. The standing time and temperature can be determined depending on the kinds and amount of detergents, and the properties of the basic proteins of interest. In addition, the standing temperature can be determined so that the basic protein solution is not frozen and the activity of protein is maintained. For examples, the temperature is 0~40° C. for histone.

After protein solution is loaded on cation exchange column, the cation exchange column is washed with the buffer solution which does not contain detergent. Thus, it is possible to remove endotoxin and detergent which are contained in the protein solution from the cation exchange column. In such step, the buffer solution for washing the cation exchange column can be the same as or different from that containing the basic proteins.

The buffer solution for eluting basic proteins of interest from the cation exchange column is different from that washing the column.

The medium composition of the present invention is as follows:

RP medium (pH 6.8): $KH_2PO_4$ 3 g/L, $KHPO_4$ 3 g/L, $(NH_4)_2SO_4$ 4 g/L, trisodium citrate 2.3 g/L, $MgSO_4$ 0.22 g/L, trace metal solution 10 m/L, Kanamycin 0.1 g/L.

Trace metal solution: ferrite citrate (III) 7.3 g/L, cobalt chloride 0.534 g/L, manganese chloride 3.2 g/L, copper chloride 0.302 g/L, boric acid 0.666 g/L, sodium molybdate 0.534 g/L, zinc acetate 1.687 g/L, thiamine 0.534 g/L, calcium chloride 11.5 g/L, trisodium citrate 20 g/L.

RS medium: RP medium, casamino acid 2 g/L

DETAILED DESCRIPTION AND THE PREFERRED EMBODIMENTS

The present invention is further explained in more detail with reference to the following examples. These examples, however, should not in any sense be interpreted as limiting the scope of the present invention.

EXAMPLE 1

To obtain gene coding Histone, H1.5. human placenta tissue 200 mg was cooled rapidly, and then was crushed in a mortar grinder. 1.2 ml of digestion solution (150 mM NaCl, 10 mM Tris-HCl (pH 8.0). 25 mM EDTA, 0.5% SDS, 0.1 mM PMSF was added to the resultant, and incubated at 50° C. for 12 hours. Then the genomic DNA was separated according to the method in "Short Protocol in Molecular biology (1992). The genomic DNA was amplified by using PCR with the following primers so as to obtain 0.7 kb product. Then, the 0.7 kb product was cut with BamH I and Xho I. Plasmid pET32a (Novagen) was cut with BamH I and Xho I, and then was ligated with the 0.7 kb product, so as to obtain pET32a-HH14.

Primers;

5'-GGTGCCAAGGATCCATGTCGGAAACCGCTCCTGCCGA-3' (SEQ ID NO: 1)

5'-GGTGCCACTCGAGTTACTTCTTTTTGGCAGCCGC-3' (SEQ ID NO: 2)

After the pET32a-HH14 was amplified by using PCR with the following primers, the product was cut with Nde I and Bam HI. PGNX4F4M was made with reference to Example 1 described in U.S. patent application Ser. No. 09/485,147, and then was cut with Nde I and Bam HI. The fragments cut with the restriction enzymes were ligated to obtain pGNX4-HH14. *E.coli* TG1 was transformed with plasmid pGNX4-HH14, and then the positive colonies were selected. The positive colonies were inoculated on RS medium, and were cultured at 30° C. for 12 hours. The culture was inoculated into 5 L fermentor (Korean fermentor Co.) contatning RS medium 1.5 L, was cultured at 30° C., at 1,000 rpm, at 1.0 vvm until that absorbance at wavelength 660 ($Abs_{660}$) was up to 60, and then, was cultured at 37° C. for 12 hours after adding lactose 30 g/L Primers:

5'-GGGCATATGATGTCGGAAACCGCTCCTGCCGA-3' (SEQ ID NO: 3)

5'-GGGGGATCCTTACTTCTTTTTGGCAGCCGC-3' (SEQ ID NO: 4)

EXAMPLE 2

The cell pellet was recovered by centrifuging 10 L of the culture solution at the rate of 5000×g for 20 minutes, and then was suspended in 50 mM potassium phosphate buffer solution (pH 8.0) containing 0.1 M NaCl to obtain 10 L of suspension. To disrupt the cell, the suspension was passed into the microfludizer (Microfludics Co.) three times at 1000 bar at speed of 400 mL/min. The disrupted cell solution was diluted at about 2.5 times with 50 mM potassium phosphate buffer solution (pH 8.0) containing 0.1 M NaCl so that $Abs_{600}$ of 10 L of the cell solution was 50. The column (100×600 mm) was filled with 900 ml of Streamline SP (Amersham Pharmacia Biotech), and was equalized with 2.5 L of solution A (200 mM NaCl+50 mM potassium phosphate buffer (pH 8.0)). After the disrupted solution was loaded on the column, and contaminants in column were removed by eluting with about 3 L of solution A so that UV value was 0. Then, the column was eluted with 2 L of solution B (500 mM Nacl+50 mM potassium phosphate buffer (pH 8.0)) so that the UV value was 0, instead of solution A. The column was eluted with 2 L of solution C (900 mM NaCl+50 mM potassium phosphate buffer (pH 8.0)) to obtain primarily purified protein solution. H1.5 protein having molecular weight of 22.449 Da was confirmed with SDS-PAGE.

The eluted solution was concentrated by ultrafiltration (cut-off 10K, Millipore) to be 500 mL solution, was concentrated again to 500 mL solution after adding potassium phosphate buffer (pH 6.8), so as to remove salt.

XK 50 column (50×300 mm, Amersham Pharmacia Biotech) was filled with 300 mL of Hydroxyapatite (Bio-Rad) type I, and was equalized with 0.5 L of 200 mM potassium phosphate buffer (pH 6.8). After 500 mL of primarily-purified concentrate was loaded on the column, contaminants in the column were removed by eluting with 0.5 L of 200 mM potassium phosphate buffer (pH 6.8) at the rate of 50 mL/min. If UV value of eluate becomes zero, contaminants bound to the column were removed by eluting with 0.5 L of 400 mM potassium phosphate buffer (pH 6.8) at the rate of 50 mL/min. To obtain 500 ml of secondarily-purified solution, the fraction containing Histone H1.5 was collected by eluting with 0.5 L of 600 mM potassium phosphate buffer (pH 6.8). The solution was concentrated by ultrafiltration (membrane with cut-off 10K, Millipore) to 100 mL of solution adding 0.5 L of 50 mM potassium phosphate buffer (pH 6.8), so as to remove salt.

XK 50 column (50×300 mm, Amersham Pharmacia Biotech) was filled with 200 mL of Poros 20 HS (PerSeptive Biosystems), and was equalized with 0.5 L of solution A. After 100 mL of secondarily-purified concentrate was loaded on the column, contaminants in column were removed by eluting with 0.5 L of solution A at the rate of 50 mL/min to zero of UV value. After contaminants bonded to the column were removed by eluting with 0.5 L of solution B, 50 ml of fraction was obtained by eluting with 2.5 L of solution B and 2.5 L of solution D (1000 mM NaCl+50 mM potassium phosphate buffer solution (pH 8.0)) at the linear gradient of solution concentration at the rate of 50 ml/min. Each fraction was analyzed by eluting the Mono S HR 5/5 column (Amersham Pharmacia Biotech) with solution B and solution D, and then the fraction having purity of 95% or higher was collected to obtain tertiary-purified solution. The solution was concentrated by ultrafiltration (cut-off 10K, Millipore) to 100 mL solution, was concentrated again into 200 mL solution adding 0.5 L of 50 mM potassium phosphate buffer (pH 6.8), and then was desalinated partially. The resultant solution was called as the tertiary-purified solution.

EXAMPLE 3

The following method is to remove endotoxin contained in tertiary-purified solution to the extremely small amount:

XK 26 column (26×200 mm, Amersham Pharmacia Biotech) was filled with SP-separose FF (Amersham Pharmacia Biotech), and was equalized with 100 mL of solution E (200 mM NaCl+50 mM potassium phosphate buffer (pH 8.0)+0.5% Triton X-114). The tertiary-purified solution 20 mL (50 mg of protein content) was agitated at 10° C. for 30 minutes after adding 0.2 mL of triton X-114(0.5% v/v) The resultant solution was loaded on the column at the rate of 5 mL/min, and then was eluted with 100 ml of solution E. Triton X-114 in the column was removed by eluting with 500 mL of solution A (200 mM NaCl+50 mM potassium phosphate buffer (pH 8.0)). 100 ml of Histone H1.5 solution was obtained by eluting with 100 mL of solution C (900 mM NaCl+50 mM potassium phosphate buffer (pH 8.0)). The eluate was dialyzed by using dialysis membrane with cut-off 10K (Spectrum Co.) to remove the salt. Purified histone powder was obtained by lyophilized 100 mL of the resultant solution. The powder had purity of 95%, and the purification yield was 35%.

The amount of endotoxin was determined by using horseshoe crab LAL (Limulus amebocyte lysate) assay according to the manufacturer's directions (Endosafe Co.). The content of endotoxin in purified histone was under 0.05 EU/mg histone.

COMPARATIVE EXAMPLE 1

20 mL of tertiary-purified solution as described Example 2 was desalted, and lyophilized Then, the content of endotoxin was measured. The content was 7.89 EU/mg histone.

COMPARATIVE EXAMPLE 2

Except that the 20 ml of tertiary-purified solution as described in Example 2 was not treated with triton X-114, the tertiary-purified solution was loaded on SP-Sepharose FF, eluted, dialyzed, desalted, and lyophilized to obtain histone powder under the same condition as described in Example 3. The content of endotoxin was 7.48 EU/mg histone.

COMPARATIVE EXAMPLE 3

XK 26 column (26×200 mm, Amersham Pharmacia Biotech) was filled with 25 mL of Aff-Pre Polymyxin Support (Bio-Rad) which is used for removing endotoxin, and was equalized with 100 mM NaCl+50 mM potassium phosphate buffer (pH 7.5). Then, 20 mL of the tertiary-purified solution as described in Example 2 was loaded on the column at the rate of 5 mlmin. The contaminant was removed by eluting with 75 ml of the same buffer solution. Then, the protein solution was collected by eluting with 50 mL of solution 200 mM NaCl+50 mM potassium phosphate buffer (pH 7.5). The solution was desalted by using dialysis and lyophilized. The content of endotoxin was 5.31 EU/mg histone.

COMPARATIVE EXAMPLE 4

XK 26 column (26×200 mm, Amersham Pharmacia Biotech) was filled with 50 mL of DEAE-Sepharose FF (Amersham Pharmacia Biotech) and was equalized with Tris buffer solution (pH 7.5). After 20 mL of the tertiary-purified solution as described in Example 2 was loaded on the column, the solution passed through was collected, desalted and lyophilized. The content of endotoxin was 7.33 EU/mg histone.

COMPARATIVE EXAMPLE 5

Filtrate which was passed through the membrane with cut-off 100K (Millipore) by ultrafilteration with 20 mL of the tertiary-purified solution as described in Example 2 was collected, desalinated by using dialysis and lyophilized. The content of endotoxin was 0.28 EU/mg histone. It was observed that some of the purified proteins were denatured.

COMPARATIVE EXAMPLE 6

Homogeneous solution was made by mixing 20 mL of the tertiary-purified solution obtained in Example 2 with 400 μl (1.0%v/v) of 50% Triton X-114 and was agitated at 4° C. for 30 minutes. The resultant solution was transferred to water bath at 37° C. and incubated for 10 minutes. The solution was centrifuged at the rate of 20,000 g at 25° C. for 10 minutes, and then the supernatant was taken. The supernatant was added by Triton X-114, and the above steps were performed two more times. The supernatant was collected. The content of endotoxin was 0.05 EU/mg histone or less. In this case, about 5% of protein was lost per a repetition step.

According to the method of the present invention, the contaminant, especially endotoxin can be removed from basic proteins which were prepared by recombinant microorganism, to an extent that it cannot be detected. In addition, the basic protein with high purity which can be obtained by removing the endotoxin according to the present invention can be used for medical use without side reaction caused by the endotoxin.

What is claimed is:

1. A method of removing endotoxin from a basic protein comprising the steps of:
   (a) adding a non-ionic detergent to a first solution containing the basic protein obtained from a recombinant microorganism to yield a resultant solution, and mixing the resultant solution,
   (b) loading the resultant solution on a cation exchange resin;
   (c) washing the cation exchange resin with a second solution that does not contain the detergent; and
   (d) eluting the basic protein from the cation exchange resin.

2. The method of claim 1, wherein said protein is one selected from a group consisting of DNA binding proteins, antibacterial basic proteins, and basic fibroblast growth factors.

3. The method of claim 2 wherein the non-ionic detergent comprises Triton X-114, Triton X-110, Tween 80 and/or Tween 20 and wherein the cation exchange resin is Streamline SF, CM-Sepharose FF, SB-Sepharose FF and/or Porus 20 HR.

4. The method of claim 3 wherein the concentration of the non-ionic detergent 0.1 to 2.0% (v/v).

5. The method of claim 1, wherein said protein is histone.

6. The method of claim 1, wherein the concentration of the non-ionic detergent is 0.01~10(v/v).

7. The method of claim 1 wherein the non-ionic detergent comprises Triton X-114, Triton X-110, Tween 80 and/or Tween 20.

8. The method of claim 1 wherein the concentration of the non-ionic 0.1 to 2.0% (v/v).

9. The method of claim 1 wherein the cation exchange resin is Streamline SP, CM-Sepharose FF, SB-Sepharose FF and/or Porus 20 HR.

10. A method of removing endotoxin from a basic protein comprising the steps of:
    (a) adding a non-ionic detergent to a first solution containing the basic protein obtained from a recombinant microorganism to yield the resultant solution, and mixing the resultant solution, wherein the resultant solution consists essentially of a buffer solution, the non-ionic detergent, and the basic protein with the endotoxin;
    (b) loading the resultant solution on a cation exchange resin;
    (c) washing the cation exchange resin with a second solution which does not contain the detergent; and
    (d) eluting the basic protein from the cation exchange resin.

11. The method of claim 10 wherein said protein is one selected from a group consisting of DNA binding proteins, antibacterial basic proteins, and basic fibroblast growth factors.

12. The method of claim 11 wherein the non-ionic detergent comprises Triton X-114, Triton X-110, Tween 80 and/or Tween 20, and the cation exchange resin is Streamline Sp, CM—Sepharose FF, SB-Sepharose FF and/or Porus 20 HR.

13. The method of claim 10 wherein said protein is histone.

14. The method of claim 10 wherein the concentration of the non-ionic detergent is 0.01 to 10.0% (v/v).

15. The method of claim 10 wherein the concentration of the non-ionic detergent is 0.1 to 2.0% (v/v).

16. The method of claim 10 wherein the non-ionic detergent comprises Triton X-114, Triton X-110, Tween 80 and/or Tween 20.

17. The method of claim 10 wherein the cation exchange resin is Streamline SP, CM-Sepharose FF, SB-Sepharose FF and/or Porus 20 HR.

* * * * *